(12) United States Patent
Gill et al.

(10) Patent No.: US 11,633,549 B2
(45) Date of Patent: Apr. 25, 2023

(54) APPARATUS, SYSTEM AND METHOD OF PROVIDING A FLUID BAG HEATER

(71) Applicants: Mary Alice Gill, St. Petersburg, FL (US); Mark Edward Sussman, St. Petersburg, FL (US); Nabel M. Ghalib, St. Petersburg, FL (US); Sai Guruva Avuthu, St. Petersburg, FL (US); Girish Satish Wable, St. Petersburg, FL (US); Ralph Hugeneck, St. Petersburg, FL (US); Ronald Harry Darnell, St. Petersburg, FL (US)

(72) Inventors: Mary Alice Gill, St. Petersburg, FL (US); Mark Edward Sussman, St. Petersburg, FL (US); Nabel M. Ghalib, St. Petersburg, FL (US); Sai Guruva Avuthu, St. Petersburg, FL (US); Girish Satish Wable, St. Petersburg, FL (US); Ralph Hugeneck, St. Petersburg, FL (US); Ronald Harry Darnell, St. Petersburg, FL (US)

(73) Assignee: JABIL INC., St. Petersburg, FL (US)

( * ) Notice: Subject to any disclaimer, the term of this patent is extended or adjusted under 35 U.S.C. 154(b) by 1354 days.

(21) Appl. No.: 15/687,683

(22) Filed: Aug. 28, 2017

(65) Prior Publication Data

US 2019/0060582 A1    Feb. 28, 2019

(51) Int. Cl.
*A61M 5/44* (2006.01)
*H05K 1/03* (2006.01)
(Continued)

(52) U.S. Cl.
CPC .............. *A61M 5/445* (2013.01); *H05B 3/34* (2013.01); *H05K 1/0393* (2013.01);
(Continued)

(58) Field of Classification Search
CPC .......... A61M 5/445; A61M 2205/3368; A61M 2205/3584; A61M 2205/3653;
(Continued)

(56) References Cited

U.S. PATENT DOCUMENTS

2002/0147426 A1* 10/2002 Faries, Jr. ............. A61M 5/445
604/113
2005/0242081 A1* 11/2005 Howick ............... B60N 2/5685
219/529

(Continued)

*Primary Examiner* — Shawntina T Fuqua
(74) *Attorney, Agent, or Firm* — Thomas J. McWilliams; Barnes & Thornburg LLP

(57) ABSTRACT

The disclosure provides an apparatus, system and method of providing a flexible heater on at least one conformable substrate of a medical fluid bag. The disclosed embodiments may include providing a matched function ink set, printed onto at least one substantially planar face of the at least one substrate to form at least: at least one conductive layer capable of receiving current flow from at least one power source; at least one resistive layer electrically associated with the at least one conductive layer and comprising a plurality of heating elements capable of generating heat upon receipt of the current flow; and at least one dielectric layer capable of at least partially insulating the at least one resistive layer.

20 Claims, 7 Drawing Sheets

(51) Int. Cl.
*H05B 3/34* (2006.01)
*H05K 1/02* (2006.01)

(52) U.S. Cl.
CPC ............... *A61M 2205/3368* (2013.01); *A61M 2205/3584* (2013.01); *A61M 2205/3653* (2013.01); *A61M 2205/50* (2013.01); *A61M 2205/8206* (2013.01); *H05K 1/0212* (2013.01); *H05K 2201/0145* (2013.01); *H05K 2201/05* (2013.01)

(58) Field of Classification Search
CPC ...... A61M 2205/50; A61M 2205/8206; H05B 3/34; H05K 1/0393; H05K 1/0212; H05K 2201/0145; H05K 2201/05
See application file for complete search history.

(56) References Cited

U.S. PATENT DOCUMENTS

| | | | | |
|---|---|---|---|---|
| 2011/0226751 A1* | 9/2011 | Lazanja | ................. | H01C 17/06 219/217 |
| 2013/0165847 A1* | 6/2013 | Scarpaci | .............. | A61M 60/113 604/28 |

\* cited by examiner

APPARATUS, SYSTEM AND METHOD OF PROVIDING A FLUID BAG HEATER

BACKGROUND

Field of the Disclosure

The disclosure relates generally to additive electronics and, more particularly, to a conformable heater for use with a fluid bag, such as for use on a medical bag.

Description of the Background

Printed electronics use printing, also referred to as "additive," methods to create electrical (and other) devices on various substrates. Printing typically defines patterns on various substrate materials, such as using screen printing, flexography, gravure, offset lithography, and inkjet. Electrically functional electronic or optical inks are deposited on the substrate using one or more of these printing techniques, thus creating active or passive devices, such as transistors, capacitors, resistors and inductive coils.

Printed electronics may use inorganic or organic inks. These ink materials may be deposited by solution-based, vacuum-based, or other processes. Ink layers may be applied one atop another. Printed electronic features may include be or include semiconductors, metallic conductors, nanoparticles, nanotubes, etc.

Rigid substrates, such as glass and silicon, may be used to print electronics. Poly(ethylene terephthalate)-foil (PET) is a common substrate, in part due to its low cost and moderately high temperature stability. Poly(ethylene naphthalate)-(PEN) and poly(imide)-foil (PI) are alternative substrates. Alternative substrates include flexible substrates, paper and textiles, although high surface texture, flexibility to bend the inks, and other factors in such substrates may present issues in printing electronics thereon. In short, it is typical that a suitable printed electronics substrate preferably has minimal roughness, suitable wettability, and low absorbency.

Printed electronics provide a low-cost, high-volume volume fabrication. The lower cost enables use in many applications, but generally with decreased performance over "conventional electronics." Further, the fabrication methodologies onto various substrates allow for use of printed electronics in heretofore unknown ways, and without substantial increased costs over conventional electronics. For example, printing on flexible substrates allows electronics to be placed on curved, conformable, or flexible surfaces, without the extraordinary expense that the use of conventional electronics in such scenarios would require.

Moreover, conventional electronics typically have lower limits on feature size. In contrast, higher resolution and smaller structures may be provided using printed electronics, thus providing variability in circuit density, precision layering, and functionality not available using conventional electronics.

Control of thickness, holes, and material compatibility are essential in printing electronics. In fact, the selection of the printing method(s) used may be determined by requirements related to the printed layers, layer characteristics, and the properties of the printed materials, such as the aforementioned thicknesses, holes, and material types, as well as by the economic and technical considerations of a final, printed product.

Typically, sheet-based inkjet and screen printing are best for low-volume, high-precision printed electronics. Gravure, offset and flexographic printing are more common for high-volume production. Offset and flexographic printing are often used for both inorganic and organic conductors and dielectrics, while gravure printing is highly suitable for quality-sensitive layers, such as within transistors, due to the high layer quality provided thereby.

Inkjets are very versatile, but generally offer a lower throughput and are better suited for low-viscosity, soluble materials due to possible nozzle clogging. Screen printing is often used to produce patterned, thick layers from paste-like materials. Aerosol jet printing atomizes the ink, and uses a gas flow to focus printed droplets into a tightly collimated beam.

Evaporation printing combines high precision screen printing with material vaporization. Materials are deposited through a high precision stencil that is "registered" to the substrate. Other methods of printing may be used, such as microcontact printing and lithography, such as nano-imprint lithography.

Electronic functionality and printability may counterbalance one other, mandating optimization to allow for best results. By way of example, a higher molecular weight in polymers enhances conductivity, but diminishes solubility. Further, viscosity, surface tension and solids content must be tightly selected and controlled in printing. Cross-layer interactions, as well as post-deposition procedures and layers, also affect the characteristics of the final product.

Printed electronics may provide patterns having features ranging from 3-10 μm or less in width, and layer thicknesses from tens of nanometers to more than 10 μm or more. Once printing and patterning is complete, post treatment of the substrate may be needed to attain final electrical and mechanical properties. Post-treatment may be driven more by the specific ink and substrate combination.

In an exemplary circumstance, medical bags, such as medical fluid or blood bags, often require heating. Typically in the known art, such heating is provided by an electronic heating hardware unit into which the medical bag must be placed. Accordingly, relatively large and/or substantially immobile equipment constitutes the manner in which heat is provided to medical fluid bags in known embodiments.

Less bulky heaters that are fabricated using atypical types of processing may provide enhanced mobility, but are typically very expensive, in part because of the complex fabrication steps needed to create such heaters, and are generally not highly reliable. Hence, these heaters are not presently applicable for use in heating medical bags.

Of course, those skilled in the art will appreciate that there are numerous additional challenges with presently used medical, and particularly intravenous fluid, bags. Such challenges include: fluid overload, such as may occur when fluids are given at a higher rate or in a larger volume than can be absorbed or excreted, which may lead to hypertension, heart failure, and pulmonary edema; hypothermia, which is induced when large amounts of cold fluids are infused, and which leads to rapid temperature changes in the heart that may precipitate ventricular fibrillation; electrolyte imbalance, in which a too-dilute or too-concentrated solution disrupts the patient's balance of sodium, potassium, magnesium, and other electrolytes; and/or an embolism, in which a blood clot or other solid mass, or an air bubble, is delivered into the circulation through an IV blocks a blood vessel.

Therefore, the need exists for a medical bag heating unit and/or bag sensing and control that allows for a more readily transportable bag, such as would take up less space in a cramped operating room, during transport on an ambulance, or the like, and that provides enhanced performance and reliability.

SUMMARY

The disclosure provides at least an apparatus, system and method of providing a flexible heater on at least one conformable substrate of a fluid bag, such as a medical fluid bag. The disclosed embodiments may include providing a matched function ink set, printed onto at least one substantially planar face of the at least one substrate to form: at least one conductive layer capable of receiving current flow from at least one power source; at least one resistive layer electrically associated with the at least one conductive layer and comprising a plurality of heating elements capable of generating heat upon receipt of the current flow; and at least one dielectric layer capable of at least partially insulating the at least one resistive layer. The matched ink set may be matched to preclude detrimental interactions between the printed inks of each of the at least one conductive, resistive and dielectric layers, and to preclude detrimental interactions with the at least one conformable substrate.

The substrate may be one of PET, flexible PVC, and polyether polyurethane. The substrate may comprise a thickness in the range of 6 mm to 10 mm. The printed inks in the matched ink set may comprise at least one positive temperature coefficient ink.

Thus, the disclosure provides a medical bag heating unit that is more readily transportable, such as would take up less space in a cramped operating room, during transport on an ambulance, or the like, and that provides enhanced performance and reliability.

BRIEF DESCRIPTION OF THE DRAWINGS

The exemplary compositions, systems, and methods shall be described hereinafter with reference to the attached drawings, which are given as non-limiting examples only, in which.

DETAILED DESCRIPTION

Figure 1:
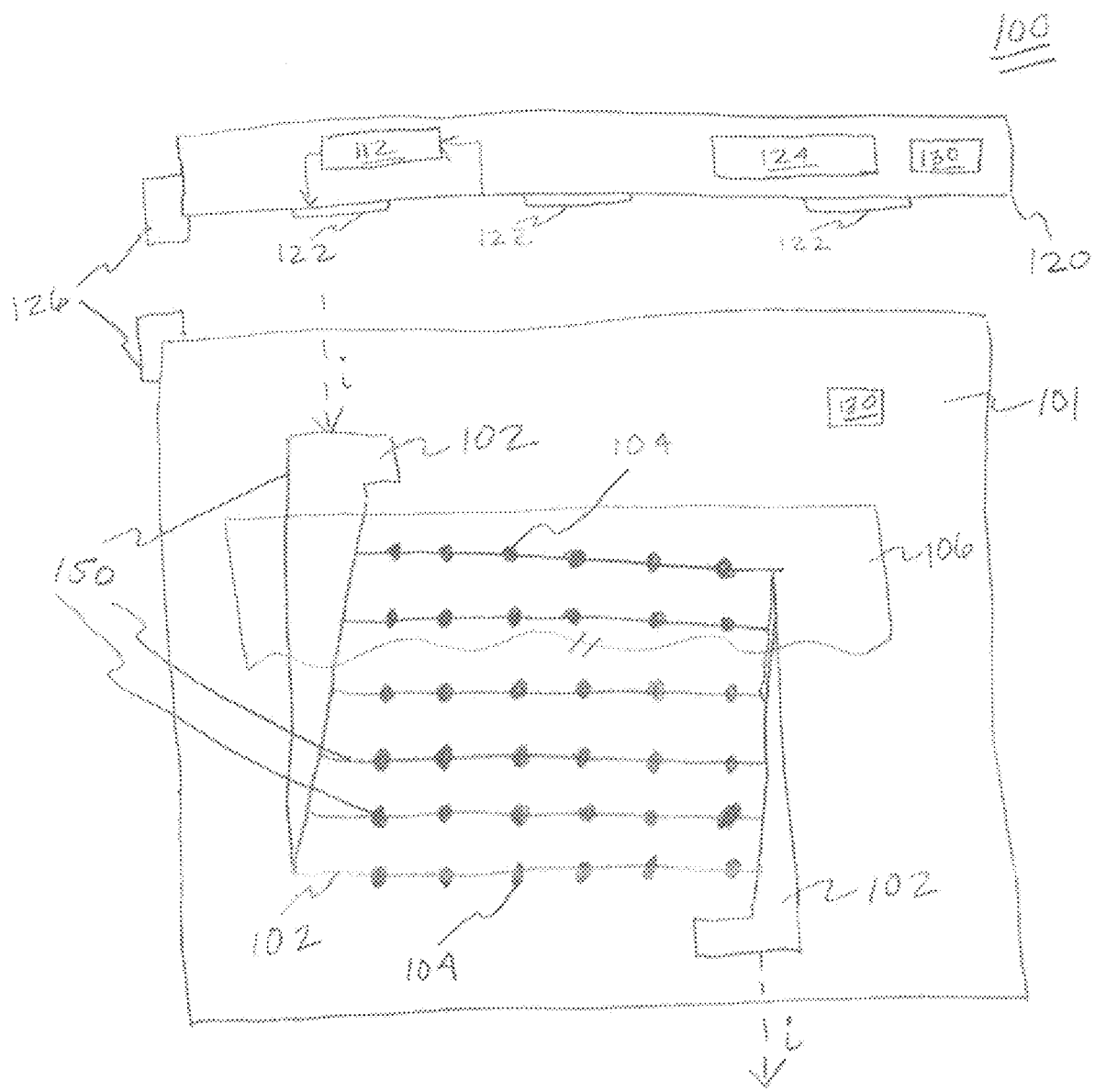
FIG. 1 is an exemplary illustration of a printed electronics heater.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that embodiments may be embodied in different forms. As such, the embodiments should not be construed to limit the scope of the disclosure. As referenced above, in some embodiments, well-known processes, well-known device structures, and well-known technologies may not be described in detail.

The terminology used herein is for the purpose of describing particular embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "upon", "connected to" or "coupled to" another element or layer, it may be directly on, upon, connected or coupled to the other element or layer, or intervening elements or layers may be present, unless clearly indicated otherwise. In contrast, when an element or layer is referred to as being "directly on," "directly upon", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the embodiments.

Historically and as discussed throughout, the formation of many small aspects of devices or small devices has generally integrated the processes of deposition and etching. That is, traces, such as conductive traces, dielectric traces, insulating traces, and the like, which include formation of device features such as wave guides, vias, connectors, and the like, have generally been formed by subtractive processes, i.e., by creating layers which were later etched to remove portions of those layers to form the desired topologies and features of a device.

Additive processes have been developed whereby device features and aspects are additively formed, i.e., are formed by "printing" the desired feature at the desired location and in the desired shape. This has allowed for many devices and elements of devices that were previously formed using subtractive processes to be formed via additive processes, including, but not limited to, printed transistors, carbon-resistive heating elements, piezo-elements and audio elements, photodetectors and emitters, and devices for medical use, such as glucose strips and ECG straps.

In short, the printing of such devices is dependent on a number of factors, including matching deposited materials, such as inks, to substrates for particular applications. This ability to use a variety of substrates may afford unique properties to printed devices that was previously unknown in etched devices, such as the ability for devices to stretch and bend, and to be used in previously unknown or inhospitable environments, such as use as sterile medical environments having limited space. By way of non-limiting example, the ability to print electronic traces on plasticized substrates allows for those substrates to remain flexible even after printing has occurred.

However, known additive properties do present limitations over the properties previously available using subtractive processing. For example, it is typical that conductive traces formed using additive processes have more limited conductivity than the conductive traces previously formed using subtractive processes. This is, in part, because pure copper traces provided using subtractive processes are presently unavailable to be printed using modern additive processing. Accordingly, some devices and elements thereof, such as heaters, may be subjected to substantial modification in order to accommodate the modified properties available using printed traces in additive processes, as compared to the use of conventional electronics-formation techniques.

In the embodiments, a large number of factors must be balanced in each unique application in order to best arrive at properties that most closely approximate those properties previously available only in subtractive processes. For example, in the disclosed devices and processes for creating those devices, compatibility must be assessed as between a substrate for printing and the receptivity of such substrate, the inks employed and the conductivity thereof, the fineness of the printed traces used, the pitch, density and consistency of the printed inks, the type of printing performed, i.e., screen printing versus other types of printing, the thickness of the printed layers, and the like. Moreover, because multiple inks may be employed in order to create the disclosed heaters, the compatibility of the inks used with one another is also an aspect of the embodiments. For example, chemical reactions between inks, different curing methodologies between inks, and the manner of deposition as between inks must all be assessed for all inks within a given ink set. Also of note, the skilled artisan will appreciate, in light of the discussion herein, that different inks within an ink set may have variable characteristics even after deposition. For example, certain inks may suffer from a valley effect in the center of a deposited trace of that ink, while peaks are created at the outer part of traces using that ink. Accordingly, because the thickness of a trace deposited using such an ink may allow for alleviation or heightening of the foregoing effect, the manner and consistency of application of each ink within an ink set is noteworthy in the embodiments.

In the known art of incorporated heaters, printed circuit boards needed to be mechanically integrated, and hence accounted for, in relation to a heater. However, the ability to use printed electronics with flexible substrates and substrates having uneven topologies may allow for printed electronics to be integrated as part of a product such as a medical bag, instead of necessitating a mechanical integration of the electronics into a standalone heater for later association with the medical bag. Needless to say, this may include the use of printed electronics onto substrates unsuitable for accepting electronics created using subtractive processes, such as the sides of a flexible medical bag. This may occur, for example, because additive processes allow for different printing types within each subsequently printed layer of the printed device, and thereby the functionality provided by each layer, such as mechanical, electrical, structural, or other functionality, may be varied as between printed layers throughout a deposition process. The skilled artisan will appreciate, in light of the discussion herein, that although the disclosure is detailed in relation to fluid bags, such as medical fluid bags, the embodiments may be employed with other products and devices having similar substrates and substrate surfaces suitable to receive a heater, particularly those with respect to which it is desirable to print the heater only after production of the product or device.

Various solutions to balance the foregoing factors, such as the prospective decreased heat produced by a printed electronics heater as compared to a common standalone heater, may be provided using additive processing. For example, printing may occur on one or both sides of a medical bag. Thereby, traces may be produced on one or both sides of the bag to form one heater unit, or series or parallel heaters. In such instances, one or more vias may be created between the sides of the bag, thus producing one heating system, or multiple heat systems on opposing sides of the bag may be connectible through or around the contents of the bag.

The embodiments provide at least a printed heater on a fluid bag substrate, such as a medical grade substrate as may be used for IV fluids, blood bags, or the like, that is formed of a layer or layers of functional ink(s), such as conductive inks, resistive inks, and insulating inks, formed into traces using additive processes to thereby effectuate the heater unit. Additional printed electronics may also be provided using the same or similar additive processes, such as electronics including sensors, antennas, such as RF, NFC, or the like antennas, thermometers, thermocouples, fluid sensors, and the like.

The embodiments may accordingly provide not only heaters for heating of fluid within a bag, but additionally sensors integrated with the bag, such as to allow for traceability, network connectivity, and patient care reporting. This traceability, connectivity, and reporting may be manual or automatic, and may be occasional, periodic, semi-continuous, and/or continuous in accordance with the embodiments. These functionalities may allow for reductions in human error in patient monitoring and reporting. For example, medical staff may be alerted by sensors associated with the bag being heated if the temperature of the bag is too high or too low, if the patient or the bag is running low on fluid, or the like.

In accordance with the foregoing, the embodiments provide patient care using less bulky heating equipment, such as to allow for optimized conditions in cramped spaces, such as operating rooms or ambulances. Further, the embodiments provide improved patient care by regulating the heating of medical fluids to ensure the fluids do not under- or overheat and cause patient discomfort, injury, or death. Moreover, integrated sensors may help to automate the patient care and care-reporting processes, and may allow for tracing, monitoring, and reporting of fluid types, medical bag chain of title, shipping and storage conditions, and the like.

Medical bags provide unique impediments to allowing for the use of additive processes, such as the printing of electronics, in association therewith. For example, because a medical bag typically has a texture associated therewith, and is highly resistant to tearing and puncture, and hence is thick and highly flexible in association with the texturing, a medical bag provides a unique substrate for additive processes. Further, a medical bag must be inert in its properties in order to allow for maintenance of sanitary conditions in association with patient care. The disclosed embodiments may be used in association with any such fluid bag, or with any other bag or substrate having such impediments to printing thereon. Furthermore, the disclosed embodiments may be used with any medical bag or any like-substrate of any size or shape.

More particularly, and as illustrated in FIG. 1, the disclosed printed electronics heater 100 may be comprised of at least three layers 102, 104, 106 additively processed onto a substrate 101. A first conductive layer 102 may provide electrodes 110 for the passing of power 112 to the heater. A second layer 104, such as may be formed of carbon or a like resistive substance, generates heat based on its resistive properties as the power 112 is applied thereto.

A third layer 106, such as in the form of a dielectric, may be provided atop at least the first two layers 102, 104, such as in order to protect against electric shock once power is applied to the bag, and in order to block the resistive layer 104 from shorting onto itself in light of the flexible nature of the bag/substrate 101, i.e., in light of the fact that the substrate provided by the bag may be folded upon itself, and/or in order to protect localized or overall overheating. Of course, the third layer 106 may additionally be provided below or between other layers 102, 104. For example, in a particular exemplary embodiment, a printed heater not including a dielectric layer 106 may be limited in operation to a temperature range of 45 to 50 degrees Celsius; but the same heater including a dielectric layer 106 may be operated in a temperature range of 45 to 65 degrees Celsius without concern that the excessive heat will pass improperly from the heater out into contact with the environment, such as a hand placed on or near the bag.

Additionally illustrated in FIG. 1 is an optional reusable cartridge 120 that may be associated with the bag/substrate 101, and which may additionally supply the power 112 and/or communicative interconnections 122 to various electronics 124 to the bag/substrate 101. The cartridge 120 may be reusable, i.e., it may be used with multiple different bags that may be interchanged from the cartridge 120. The cartridge 120 may physically associate with the bag via any known removable connection 126, such as clips, a snap or latch, Velcro, or the like. Alternatively, the cartridge 120 may permanently attach to the bag.

The cartridge 120 may house therewithin a variety of electronics 124, such as including a power supply 112 for the bag heater 100 and/or for sensors 130 associated with the bag and/or included within cartridge 120. As used herein, such sensors 130 associated with the bag and/or the cartridge may include any known sensors, such as fluid level sensors, temperature sensors, pressure sensors, vibration sensors, resistivity sensors, conductivity sensors, antennae, and the like. The sensors 130 may interconnect to the cartridge 120, if not resident therein, via interconnects 122. Additionally and as will be apparent to the skilled artisan in light of the discussion herein, not only may the disclosed sensors 130 be printed on the bag along with the disclosed heater layers 102, 104, 106, but the sensors 130 may also be placed on the bag via other known methodologies such as by lamination, and/or may be included within the cartridge 120.

That is, additional sensors, integrated circuits, memory, and the like may be associated with the cartridge 120, may be printed on the substrate 101 via the disclosed or other methodologies, and/or may be formed on or in distinct systems associated with the cartridge 120 or the substrate 101. It goes without saying that any elements printed on substrate 101 may be discrete from the heater 100 elements, but may nevertheless be similarly conformable to the flexible substrate 101.

Moreover, the embodiments may include additional layers (not shown) to those discussed above. For example, a secondary substrate (not shown) may be provided in the form of a highly adhesive sticker, wherein the sticker may or may not provide a substrate suitable for receiving printed electronics on one side of the "sticker." In such an instance, the compatibly adhesive surface may be applied to the opposing face of the sticker, such as via additive process printing, lamination, deposition, or the like, such as for eventual adhesion to the bag substrate 101. Of note in such instances, the adhesive layer should be suitable to pass the heat from the heater layer through the adhesive and through the bag substrate to the contents of the fluid bag.

Further, either the bag or a multi-use cartridge 120 associated therewith may include electronics 124 comprising one or more circuits and/or integrated circuits, such as memory circuits, control circuits and/or communication circuits. Accordingly, not only may the use, shipping, and storage conditions of the bag be monitored in real time, such as by sensors 130, but the data may also be collected and stored, either on the bag or off the bag on an integrated circuit memory device. For example, each bag may have an aging cycle, wherein the ink, heating system, stickiness to the bag, connectivity to power, and like factors may decay over time or use such that a bag's aging cycle may limit its, or the associated heater's, usefulness over time. Moreover, communication circuits, such as cellular, RF, WiFi, Bluetooth, NFC, or other known communication circuits, such as may be embedded in the cartridge and/or otherwise associated with the heater 100, may allow for this or any other data to be sent remotely outwardly from the bag. This remote sending, and other functionality associated with the bag and the cartridge, may include and/or be controlled by one or more control circuits within electronics 124.

For example, the control system(s), may allow for a change in heater or bag content temperature automatically or manually, as referenced throughout. Accordingly, the control system(s) may direct the communication circuits, such as via Bluetooth, radio-frequency (RF), near-field communications (NFC), or the like, to communicate with a secondary controlling device, such as an app on a mobile device.

The power source 112 that delivers power to the heating system 100, such as through or at the direction of the control circuit, may be via a battery (onboard or off), or a primary power source, such as via A/C wall outlet power run through a voltage stepper. A battery may be a rechargeable, removable, replaceable, or permanent battery, by way of non-limiting example. Power source(s) 112 may work in conjunction with the aforementioned control circuits to deliver power only upon particular triggers, such as the contents of a bag falling below a particular temperature threshold. That is, variability in heat levels, such as may be indicated by the control circuit(s), may be made manually by a user or automatically based on system characteristics.

In order to associate the printed electronic layers with substrate 101, ink sets 150 may be selected in light of process parameters to form the heater 100 and the operation environment in which the bag will be used. For example, not only is application and curing of each ink important in light of the function to be imparted to the bag, but additionally the effects of operating conditions on each ink must be considered. In short, material compatibility must be maintained, and a chemical inertness must be present between the additive process elements. By way of nonlimiting example, the ink solvents used in relation to the inkset 150 must be inert with respect to both the bag, and the sanitary nature and operating environment of the bag. Further, sterilization of the bag using radioactive or ultraviolet processes must not degrade the printed electronic materials in the inkset 150 or the functionality provided thereby. Yet further, the surface energy of the substrate must be matched to the applied inks, layers, and/or coatings of the inkset 150 and onto the substrate 101. Additionally, the curing temperatures of any inks or layers in the inkset 150 applied to the bag must be considered in light of the melting or degradation temperature of the bag itself. For example, bags formed of certain polymers cannot be subjected to heat levels sufficient to cure certain types of frequently used printed electronic inks.

In order to address certain of the foregoing of the concerns and yet obtain sufficient curing of the ink and additive process layers, different types of curing methodologies may be used in the embodiments. For example, convection curing using a convection box or conveyor belt may be used to apply sufficient curing energy; likewise, infrared or near infrared energy may be applied; additionally, ultraviolet curing may be used; and photonic curing may also be employed. Yet further, ramping temperatures may be used in order to provide sufficient levels of curing, such as wherein high or low temperatures are employed to improve the ability of the bag substrate to withstand more heat or energy than might otherwise be the case.

Thus, the embodiments provide a heater for heat transfer and heating control to and into a fluid bag. In order to obtain this functionality, a variety of inks in inkset 150 may be employed. For example, Henkel Ink's 56A-silver and 1010-silver may be employed. Further, ink ECI8001 of positive thermal coefficient carbon may be employed as a self-limiting temperature ink. Yet further, Henkel Ink 455B may be used as the aforementioned dielectric. Additional inks may include EMS/ECM Inks CL1021 and 2051.

Any of the variety of available fluid bags may provide the substrate 101 for the printed electronic heater 100 discussed herein. Such bags, and hence substrate 101, may be formed of, for example, PET, flexible PVC, polyether polyurethane, or the like, and may vary between for example, 6 mm and 10 mm in thickness. In light of the referenced exemplary inks of inkset 150 and exemplary substrates 101, the power supplied 112, such as via the cartridge 120 discussed herein, may be between 9 and 12 volts, and may particularly be 10 volts.

Further, various screen mesh characteristics must be considered in order to allow for printing of layers 102, 104, 106, and/or other elements, such as aspects of sensors 130, onto substrate 101. For example, different thicknesses, i.e., wires per unit area, of mesh must be considered, as must be different thickness of the wires forming the mesh; the transference of ink through the mesh, such as may cause calendaring of the ink, must also be considered; stencil printing versus screen printing is an additional consideration. The mesh must also be considered in light of ink characteristics within inkset 150, such as viscosity, emulsion, and solvent type. Specifically and by way of non-limiting example, a mesh having a mesh opening with 4-6 times the diameter of the print particles may be employed.

Figure 2:
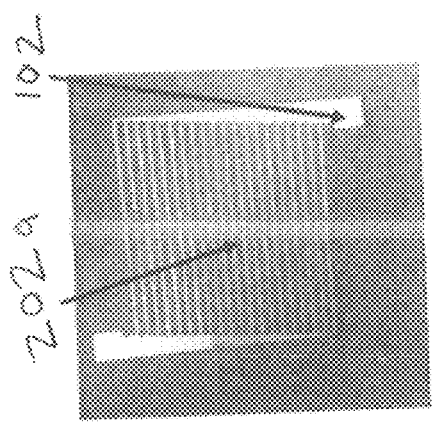
FIG. 2 is an illustration of a printing screen that may be used to print disclosed aspects onto a substrate.
Figure 3:
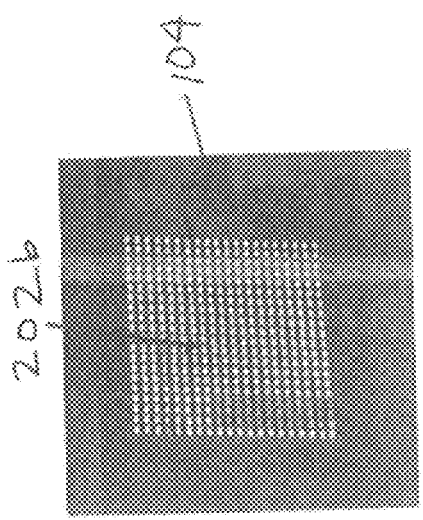
FIG. 3 is an illustration of a printing screen that may be used to print disclosed aspects onto a substrate.
Figure 4:
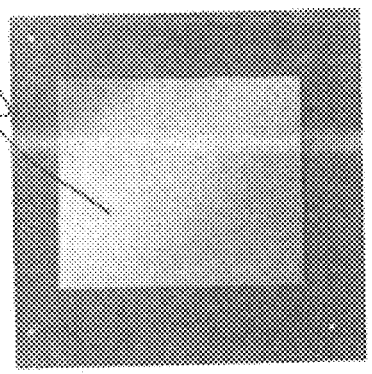
FIG. 4 is an illustration of a printing screen that may be used to print disclosed aspects onto a substrate.

As illustrated in FIGS. 2, 3, and 4, a variety of screens 202a, 202b, 202c may be used to print the various layers 102, 104, 106 and other printed aspects, such as sensors 130, discussed herein onto the medical bag. As illustrated, such screens may include screens 202a for the electrodes and bus bars, i.e., conductive layer 102; screen 202b for the heater elements, i.e., resistive layer 104; and screen 202c for the dielectric layer 106 applied atop the electrodes, bus bars, and heater elements. In an exemplary embodiment, the electrode screen 202a may be a silver screen formed of stainless steel and having a mesh of 270. The heater element screen 202b may a carbon screen comprised of polyester and having a mesh of 230. The dielectric screen 202c may be formed of stainless steel and may be a mesh of 280.

As referenced above, the nature of the substrate 101 as a fluid bag may limit the ability to dry and cure the inks of inkset 150 after the inks are applied using the above-referenced or other screens. In an exemplary process, the silver and carbon ink printing may be run at 100-120 degrees Celsius for 6-10, such as 8, minutes to avoid degradation of the bag. Further, UV curing may occur, either distinct from or in conjunction with the 120 degrees Celsius drying, such as at 45-70%, such as 60%, intensity for a limited time.

Of course, the referenced drying temperature ranges of 100 to 120 degrees Celsius may have different effects on different substrates 101. For example, shrinkage may occur, such as only in an initial or in consecutive curing cycles. Moreover, certain substrates, such as those having decreased thickness, may experience wrinkles during curing if not held flat, such as in a vacuum fixture, and thinner substrates may further experience additional degradation, including undue stresses on the applied inks due to the heating of the substrate during curing.

Certain parameters may allow for optimal performance of a printed heater in accordance with the disclosure. For example, printed electrodes of heating layer 104 having resistivity of 3-6 ohms may be desirable. Further, power output of the heating elements of heating layer 104 may be improved, such as to approximately 1.5 amps, due to the application of the dielectric layer 106, where present. Moreover, increased heating power output may be obtained by running heaters 100 in series and/or in parallel, such as on opposing sides of a medical bag. For example, vias, pass-throughs, and/or different connectors may additionally be provided not only to connect heating elements to external power sources, but also to connect any parallel or series heating elements, including those that may be formed on both sides of the bag in order to optimize delivery of heat. In embodiments, the connection of two heating elements in parallel, as discussed hereinabove, does not cause a drop in operating temperature, i.e., both heating systems may maintain a 55 to 60 degree Celsius temperature range.

Further, it will be appreciated by the skilled artisan in light of the discussion herein that the temperature drop from one side of the medical bag substrate 101 to the other, i.e., the heat that reaches the contents of the medical bag, may vary based on the composition of the medical bag. In certain embodiments, it has been assessed that the temperature drop from the heater side of the substrate 101 to the content side of the substrate 101 may be maintained in the range of approximately a 5 degree Celsius drop, and, dependent on the substrate, should reasonably be in the 1 to 10 degree Celsius range.

In embodiments, the power 112 delivered to the heater 100, such as from the associated cartridge 120 discussed herein or from any external power unit electrically connected to the conductor layer 102, may be in the range of 10 to 30 watts. Needless to say, this power may be ramped through an associated range of delivered power, such as in order to avoid detrimental effects on the heater or bag contents. Minimal ramp up time may be available through the use of the disclosed embodiments, such as in the range of 2 to 10 seconds, and more particularly approximately 5 seconds, to a uniform temperature above 35 degrees Celsius. In such a power operating range and for a bag having a content volume of approximately 0.5 liters of H2O, the temperature of the bag contents may be raised in the range of 5 to 15 degrees Celsius, such as over approximately 4 hours of heating element operation, using the exemplary embodiments discussed herein. It goes without saying the decreased power may be delivered if the bag contents are merely to be maintained at a certain temperature, rather than being increased in heat level.

As referenced above with respect to the substrate printing process, in operation the bag or similar substrate may provide a limiting characteristic. For example, although a flexible, textured surface substrate, such as an Argotech ST3655, may have formulated thereon a heating system using, for example, combinations of EMS silver and carbon inks, and/or Henkel Inks, such as Henkel 1010N56A, the heat delivered by such system may reach in the range of 70 to 100 degrees Celsius, and a typical substrate of a medical bag may break down under such high temperatures. For example, a blood bag made by Nypro of Massachussetts may burn or melt under such conditions, and even if the bag integrity is maintained, optimal heat transfer may not occur to the contents of the bag from the heating element in the event the temperature of the heating element is sufficiently high so as to have detrimental effect on the integrity of the bag. Thus, an inkset 150 comprised of positive temperature coefficient inks, or other manner of engaging in temperature control of the heating layer 104, may be provided to maintain heat levels at acceptable but sub-maximal ranges.

More particularly, an Argotech ST3655 bag may prove usable with a large number of inks, and may allow for those inks to provide acceptable electrical and thermal performance. Certain inks disclosed herein, such as Henkel Ink ECL1010, may be used in the embodiments, although flexible inks, Henkel Ink ECL56A may provide optimal performance based on the flexible bag characteristics. Additional operating considerations include that the heat output and transfer through the bag substrate, and the performance and efficiency of the ink traces formed of inksets 150, may change as fluid levels increase and decrease within the bag.

In alternative embodiments, approaches may be taken in printing the heater to more efficiently encapsulate and trap the heat and redirect it back through the substrate. For example, a suitable heat transfer layer, such as a preliminary dielectric layer, may be printed on the substrate 101 to improve heat transfer from the heater printed thereupon, and/or to provide a more receptive printing surface for the inks of inkset 150. Moreover, refined control systems, such as may be resident in the cartridge 120 discussed throughout, and/or fixed resistance or positive temperature coefficient inks, may also be provided to maintain power levels and heat levels.

For example, a positive temperature coefficient (PTC) heater may provide a self-regulating heater. A self-regulating heater stabilizes at a specific temperature as current runs through the heater. That is, as temperature is increased the resistance of the self-regulating heater also increases, which causes reduced current flow and, accordingly, an inability of the heater to continue increasing in temperature. On the contrary, if the temperature is reduced, the resistance decreases, thereby allowing more current to pass through the device. In a typical embodiment, a self-regulating/PTC heater thus provides a stabilized temperature that is independent of the voltage applied to the heater.

Figure 5:
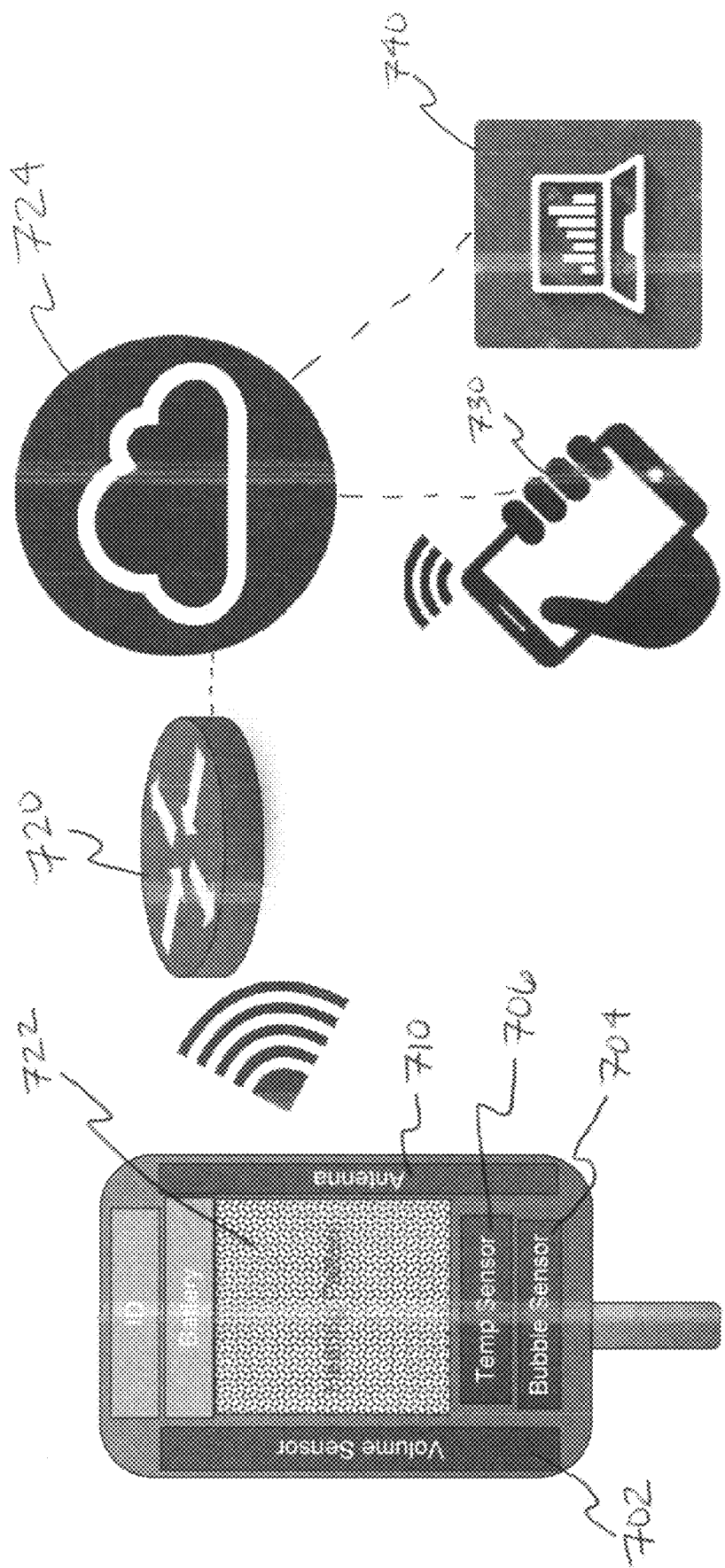
FIG. 5 is an illustration of a networking embodiment of the disclosure.

That is, and by way of the non-limiting example set forth with respect to FIG. 5, the disclosure may provide a smart medical, such as an IV, bag. The bag may include one or more sensors, such as volume sensor 702, bubble sensor 704 and temperature sensor 706, that may be associated with on-board control as discussed above, and/or which may be subjected to off-board communications, such as via antenna 710. Control and data signals may be exchanged, such as via the antenna 710, with a data gateway 720, which may ensure secure data exchange over, for example, the cloud 724, with one or more manual or automated control systems, such as a mobile device 730, computing device, server, or the like 740.

Accordingly and based on sensed data by temperature sensor 706, this control may, for example, ensure heating pattern 722 heats the fluid within the bag to, and/or maintains the temperature at, a proper set point. Likewise, the volume/fluidics sensor 702 may measure the volume of the remaining solution, and by doing that on a regular basis measure the amount of fluid provided over time, and may convey this data to the control 730, 740 to allow for monitoring and modification. Yet further, bubble sensor 704 may measure and convey, such as wirelessly using antenna 710, the size and amount of bubbles, to allow for proper control thereof. Of course, various other sensors may be associated with the bag and communicative over antenna 710, such as a sensor that registers the type of fluid and its the expiry date, by way of non-limiting example.

Figure 6:
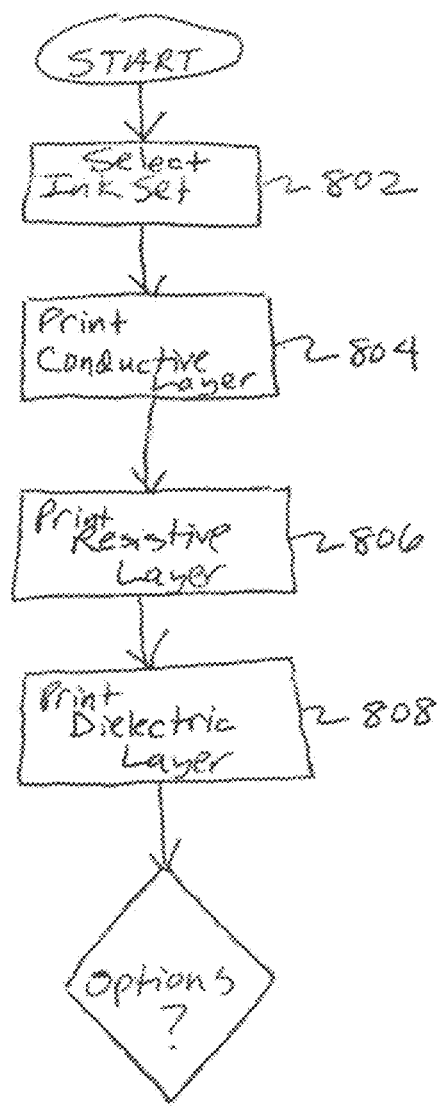
FIG. 6 is a flow diagram illustrating a method of providing a conformable heater system, such as on a medical fluid bag.

In accordance with an embodiment such as that of FIG. 5, data may be received by an application on a mobile device (Smartphone/PC/Tablet) 730 via the data gateway 720, such that a healthcare professional may manually control sensed aspects of the bag via interaction with the application. Accordingly, the sensor data may be displayed in the application in a way that the healthcare professional may readily interpret the data easily. The application may additionally include alarm features to alert a healthcare professional if something goes awry, i.e., too many/too big bubbles, temperature out of range, fluid flowrate out of range, fluid expired, etc. Needless to say, such data reception and control output may also be automated in the embodiments. FIG. 6 is a flow diagram illustrating an exemplary method 800 of providing a conformable heater, such as on a medical bag substrate. At step 802, an ink set is inter-matched for use to print compatible ink layers within the ink set, and is matched to the receiving organic or inorganic conformable substrate that is part of a medical fluid bag. At step 804, a conductive layer formed of at least one ink from the ink set is printed on the substrate.

At step 806, a resistive layer is printed from the ink set, wherein the resistive layer provides at least a plurality of heating elements in electrical communication with the conductive layer. At step 808, a dielectric layer is printed from the ink set in order to insulate the conductive and resistive layers.

At optional step 816, the heater may be removably and electrically connectively associated with one or more cartridges having circuits, such as control systems and communication systems, resident therein, and with one or more power source connections to allow for power to be supplied to the heating elements via the conductive layer. By way of example, step 816 may include the printing or other manner of interconnecting of one or more electrical interconnections from the cartridge over the substrate and to the heater.

Figure 7:
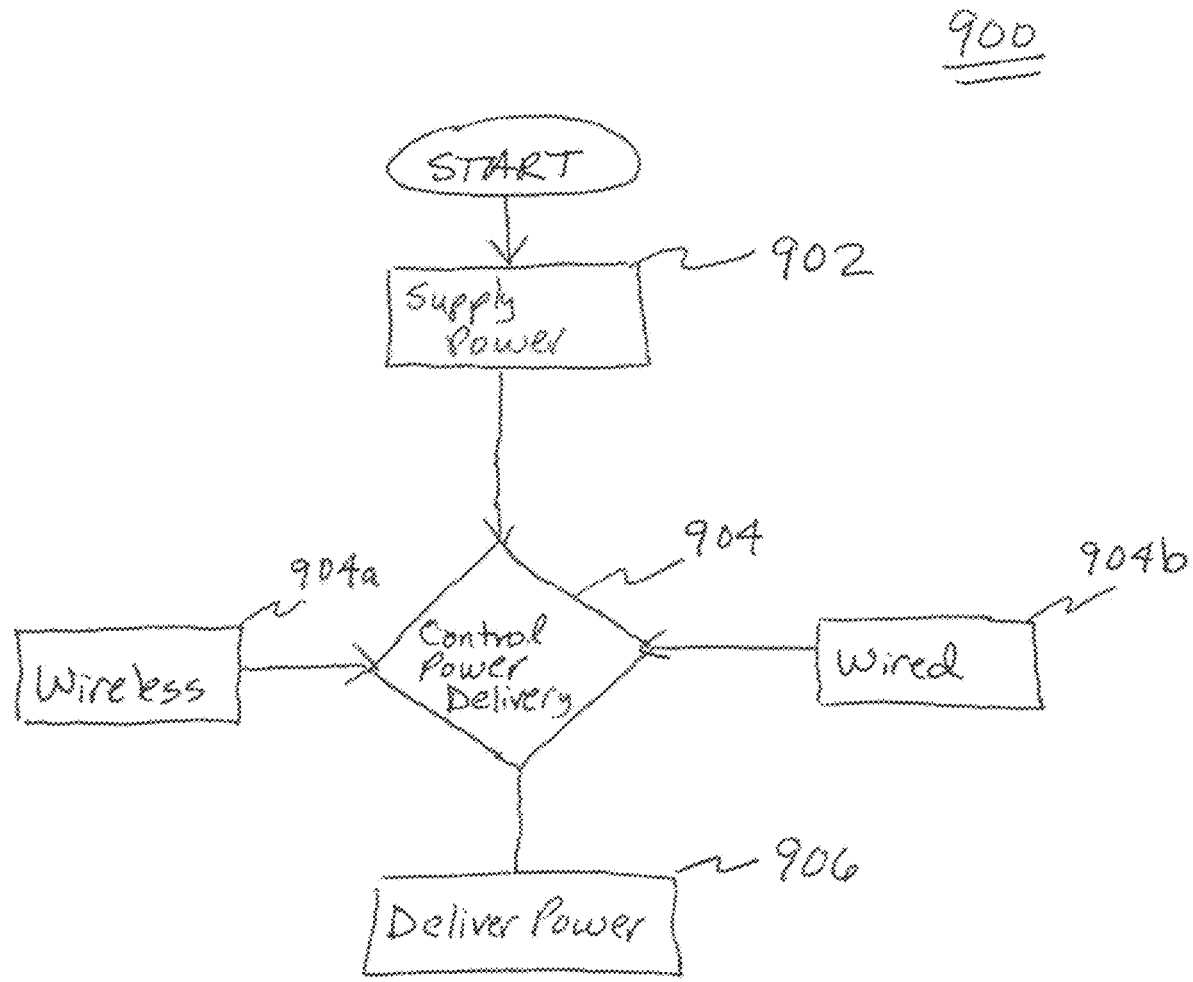
FIG. 7 is a flow diagram illustrating a method of using a conformable heater system.

FIG. 7 is a flow diagram illustrating a method 900 of using a conformable heater system. In the illustration, the conformable heater may be associated with a power source at step 902. This association may include a permanent association, such as via "plugging in" or recharging of a permanently embedded battery, or a removable association, such as wherein an external power source, such as a battery, a mobile device, or the like, may be removably associated with the heater, including via a cartridge.

At step 904, the delivery of power from the power source to the heater may be variably controlled. Optionally, at step 904*a*, wireless control may be via a wireless connection, such as from a mobile device to the control circuit. This wireless, or a wired, connection may be controllable using a user interface provided by an "app" on the mobile device, by way of non-limiting example. The control provided thereby may be automated based on predetermined triggers or operational limitations, manual, or a combination thereof. Wireless control may be provided over any known type of wireless interface.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:

1. A flexible heater formed on at least one conformable substrate of a medical fluid bag, comprising:
   a matched function ink set, printed onto at least one substantially planar face of the at least one substrate to form at least:
   at least one conductive layer capable of receiving current flow from at least one power source, having a cartridge physically and electrically associated with the at least one conductive layer;
   at least one resistive layer electrically associated with the at least one conductive layer and comprising a plurality of heating elements capable of generating heat upon receipt of the current flow; and
   at least one dielectric layer capable of at least partially insulating the at least one resistive layer;
   wherein the matched ink set is matched to preclude detrimental interactions between the printed inks of each of the at least one conductive, resistive and dielectric layers, and to preclude detrimental interactions with the at least one conformable substrate.

2. The flexible heater of claim 1, wherein the substrate comprises an inorganic substrate.

3. The flexible heater of claim 1, wherein the substrate comprises one of PET, flexible PVC, and polyether polyurethane.

4. The flexible heater of claim 3, wherein the substrate comprises a thickness in the range of 6 mm and 10 mm.

5. The flexible heater of claim 1, wherein the detrimental interactions occur during at least one of deposition and curing of the printed inks.

6. The flexible heater of claim 1, wherein the printed inks in the matched ink set comprise at least one positive temperature coefficient ink.

7. The flexible heater of claim 1, wherein the medical fluid bag comprises a blood bag.

8. The flexible heater of claim 1, further comprising two of the at least one conformable substrates on opposing faces of the medical fluid bag, each having thereon a one of the flexible heater.

9. The flexible heater of claim 1, wherein the two flexible heaters are electrically connected by at least one of a trace around, a via, and a pass through.

10. The flexible heater of claim 1, further comprising a control circuit connectively associated with the cartridge.

11. The flexible heater of claim 10, wherein the control circuit controls an amount of heat delivered by the heating elements.

12. The flexible heater of claim 11, wherein the control system comprises a wireless receiver.

13. The flexible heater of claim 12, wherein the wireless receiver comprises at least one of a Bluetooth, WiFi, NFC, cellular and RF receiver.

14. The flexible heater of claim 11, wherein a wirelessly linked remote portion of the control system comprises a mobile device app.

15. The flexible heater of claim 10, further comprising at least one power source connectively associated with the control circuit.

16. The flexible heater of claim 15, wherein the power source comprises one of a rechargeable battery and a power outlet plug.

17. The flexible heater of claim 1, wherein the physical and electrical connection comprise removable connections.

18. The flexible heater of claim 17, wherein the removable physical connections comprise at least one of clips, snaps, latches and Velcro.

19. The flexible heater of claim 1, wherein the dielectric layer insulates ones of the plurality of heating elements from shorting onto one another due to the conformability of the conformable substrate.

20. The flexible heater of claim 1, wherein the dielectric layer insulates heat produced by the heating elements to avoid localized overheating.

\* \* \* \* \*